United States Patent
Kim et al.

(10) Patent No.: US 10,045,792 B2
(45) Date of Patent: Aug. 14, 2018

(54) TOOL FOR SURGICAL OPERATION USING ULTRASONIC WAVES

(76) Inventors: Song Yee Kim, Gyeonggi-do (KR); Sa Im Kim, Seoul (KR); Soo Jung Kim, Seoul (KR)

(*) Notice: Subject to any disclaimer, the term of this patent is extended or adjusted under 35 U.S.C. 154(b) by 277 days.

(21) Appl. No.: 14/378,947

(22) PCT Filed: Feb. 16, 2012

(86) PCT No.: PCT/KR2012/001183
§ 371 (c)(1),
(2), (4) Date: Aug. 14, 2014

(87) PCT Pub. No.: WO2013/122274
PCT Pub. Date: Aug. 22, 2013

(65) Prior Publication Data
US 2015/0025557 A1    Jan. 22, 2015

(51) Int. Cl.
*A61B 17/32*   (2006.01)

(52) U.S. Cl.
CPC ........... *A61B 17/320068* (2013.01); *A61B 17/320092* (2013.01); *A61B 2017/320072* (2013.01)

(58) Field of Classification Search
CPC .... A61B 17/320068; A61B 17/320092; A61B 2017/320072; A61B 2017/320076;
(Continued)

(56) References Cited

U.S. PATENT DOCUMENTS 6,129,735 A * 10/2000 Okada ........... A61B 17/320068
606/169
6,458,142 B1 * 10/2002 Faller ............. A61B 17/320068
604/22
(Continued)

FOREIGN PATENT DOCUMENTS

JP    2000-041990 A    2/2000
JP    2000-051226 A    2/2000
(Continued)

OTHER PUBLICATIONS

International Search Report dated Oct. 23, 2012 for PCT/KR2012/001183.

*Primary Examiner* — Ryan J Severson
*Assistant Examiner* — Christian Knauss
(74) *Attorney, Agent, or Firm* — Scott H. Davison; Musick Davison LLP

(57) ABSTRACT

A tool for surgical operation using ultrasonic waves is provided. The tool includes a transducer generating ultrasonic waves, a cylindrical bar-shaped transmitting rod for transmitting the ultrasonic waves, an end effector for cutting a surgical site using the ultrasonic waves transmitted from the transmitting rod, extended from one end of the transmitting rod, in which a part of the circular cross-sectional area thereof is flatly formed from the point corresponding to a second vibration node so as to allow gain step to start at the second vibration node, a rod cover for encompassing the transmitting rod using, as connection points, a plurality of vibration nodes formed when ultrasonic waves are transmitted through the transmitting rod, and a jaw for holding the surgical site while engaged with the end effector, is combined to one end of the rod cover in a pivotable manner, and is positioned to face the end effector.

9 Claims, 9 Drawing Sheets

(58) Field of Classification Search
CPC ....... A61B 2017/320073; A61B 2017/320074; A61B 2017/320075; A61B 2017/320077; A61B 2017/320089; A61B 2017/32009
See application file for complete search history.

(56) References Cited

U.S. PATENT DOCUMENTS

| | | | |
|---|---|---|---|
| 6,790,216 B1* | 9/2004 | Ishikawa | A61B 17/320068 606/169 |
| 2002/0029054 A1* | 3/2002 | Rabiner | A61B 17/320068 606/169 |
| 2002/0077644 A1* | 6/2002 | Beaupre | A61B 17/320068 606/169 |
| 2007/0239153 A1* | 10/2007 | Hodorek | A61B 90/10 606/41 |
| 2007/0282333 A1* | 12/2007 | Fortson | A61B 17/320092 606/50 |
| 2009/0216228 A1* | 8/2009 | Masuda | A61B 17/320092 606/48 |

FOREIGN PATENT DOCUMENTS

| | | |
|---|---|---|
| JP | 2002-065688 A | 3/2002 |
| JP | 2004-313342 A | 11/2004 |
| KR | 10-0821500 B1 | 4/2008 |
| WO | 2009141616 A1 | 11/2009 |

\* cited by examiner

[Fig.1]
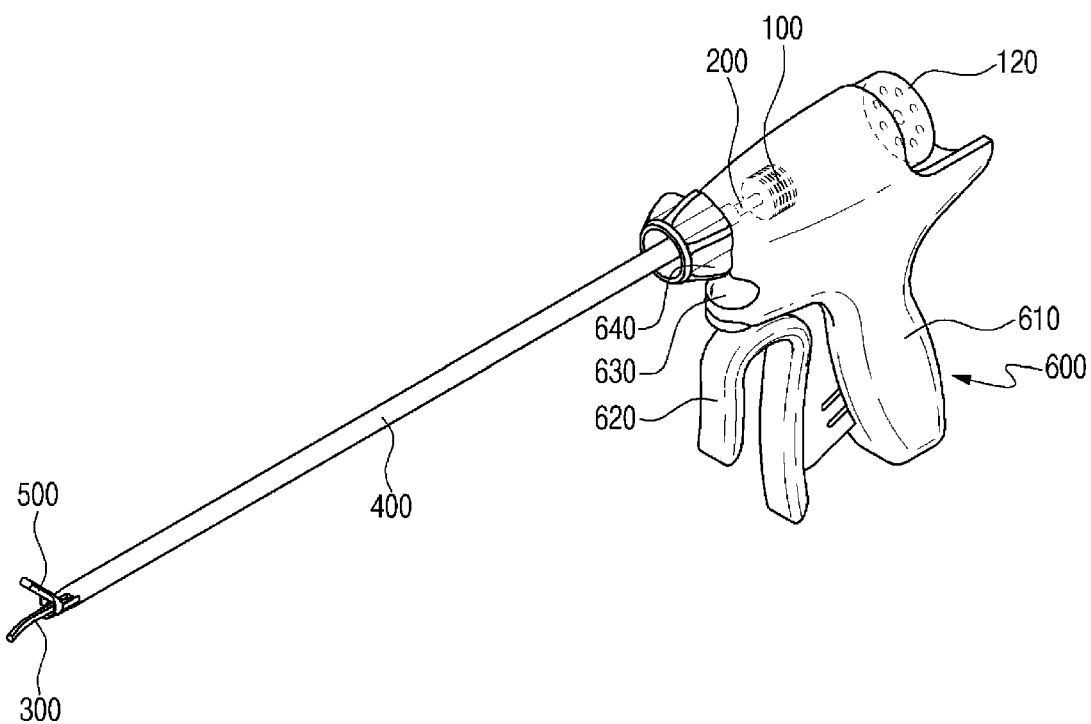

[Fig.2]
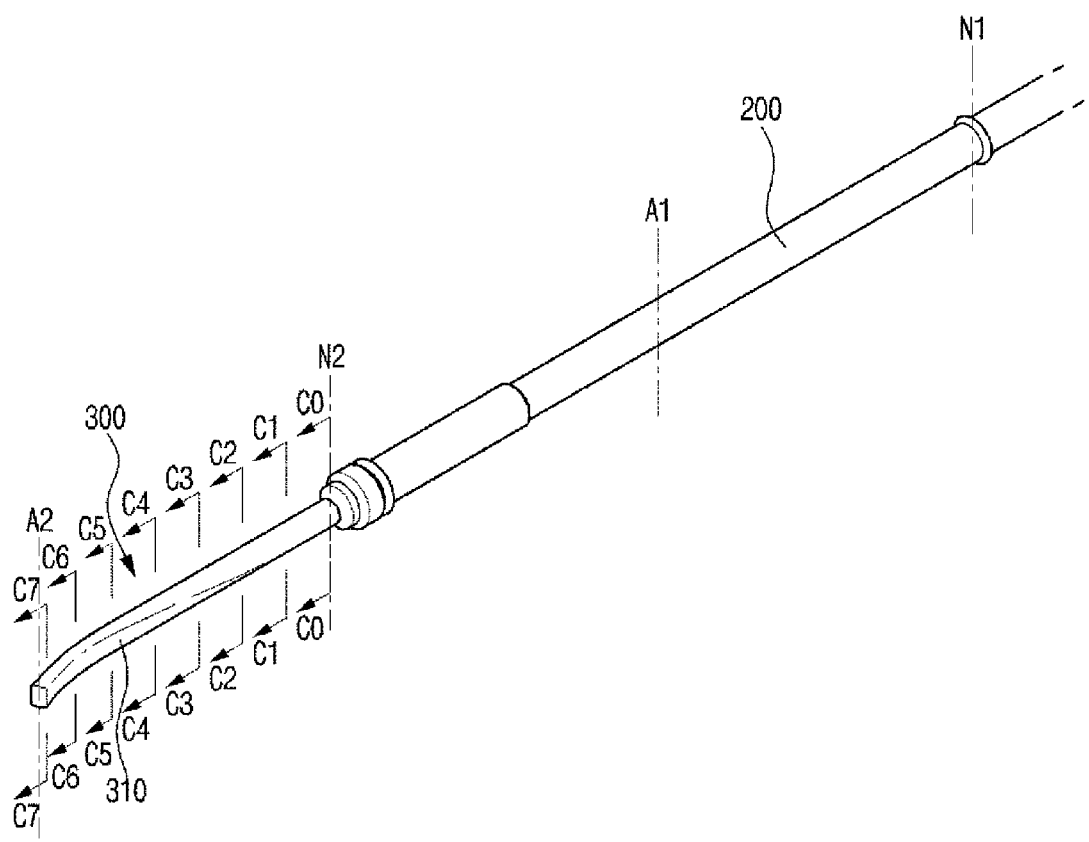

[Fig.3]
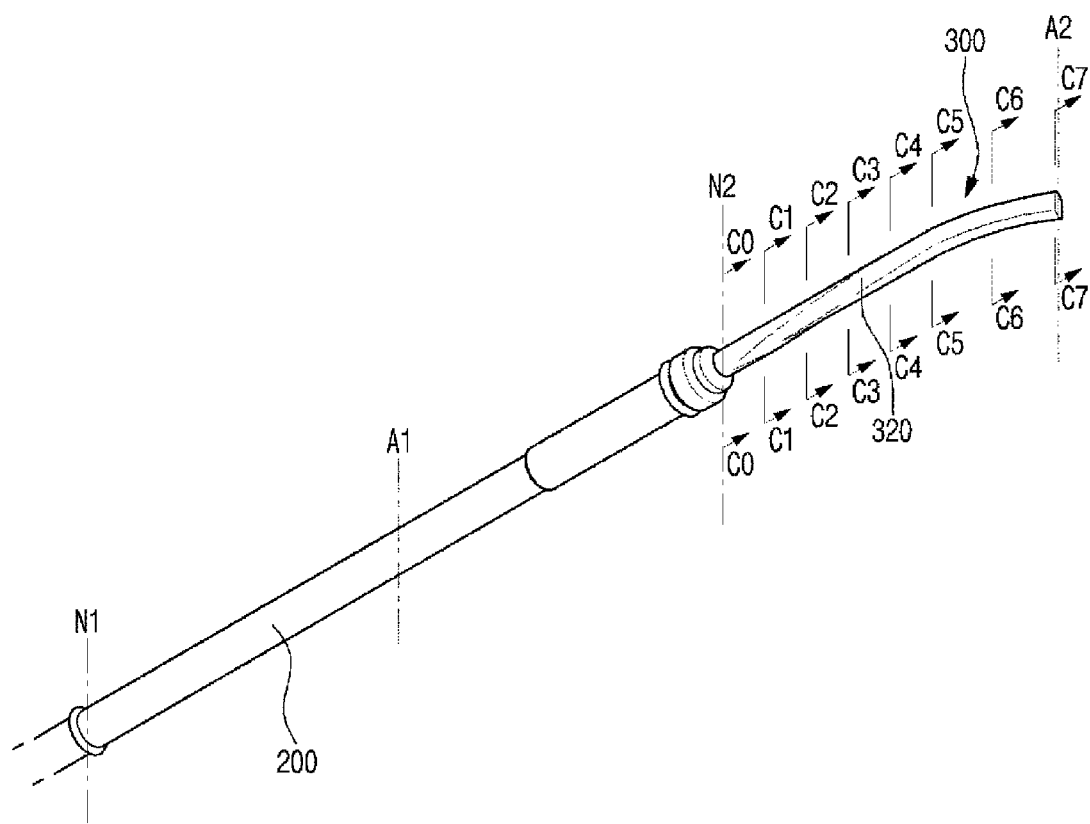

[Fig.4]
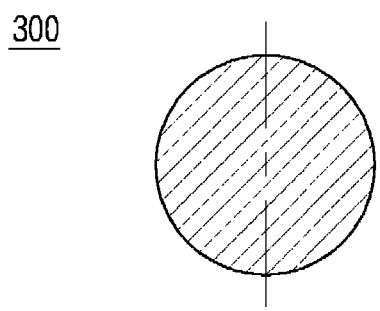
[Fig.5]
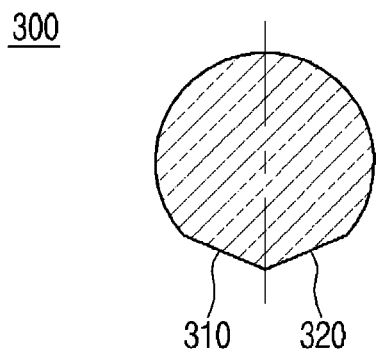
[Fig.6]
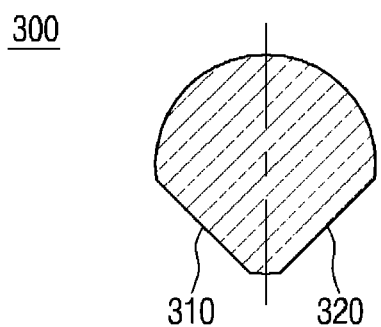

[Fig.7]
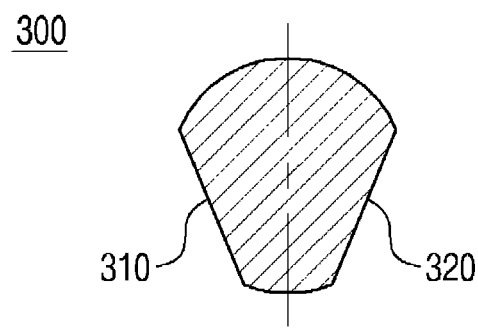
[Fig.8]
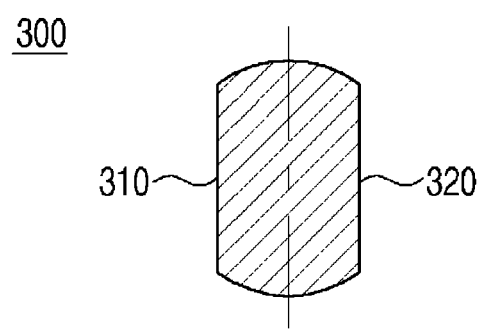
[Fig.9]
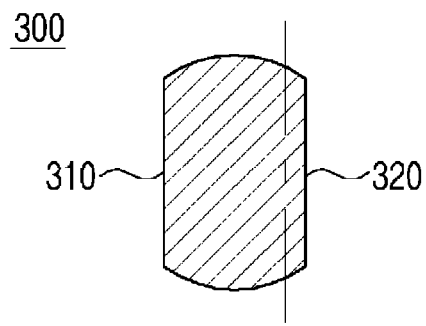

[Fig.10]
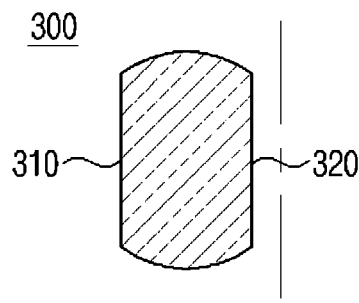
[Fig.11]
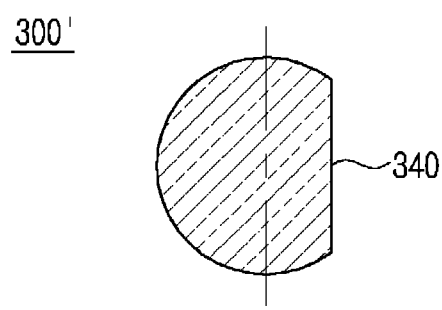
[Fig.12]
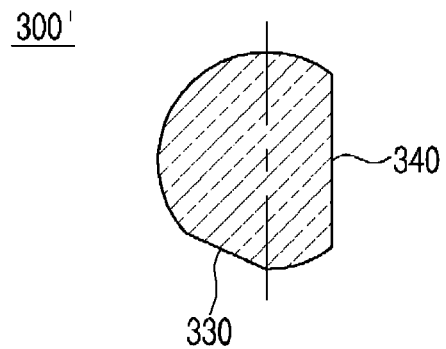

[Fig.13]
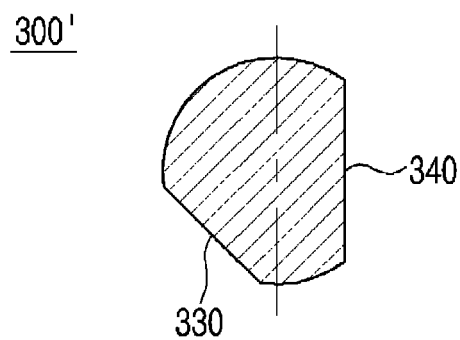
[Fig.14]
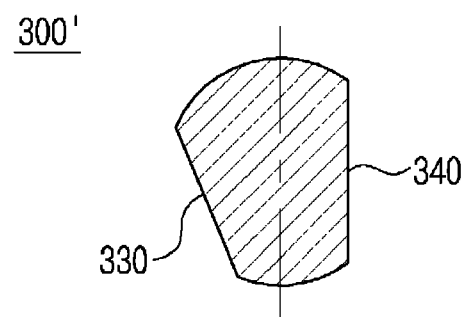
[Fig.15]
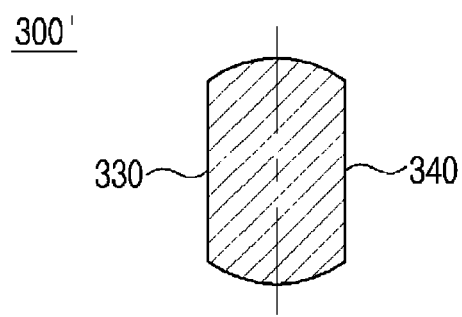

[Fig.16]
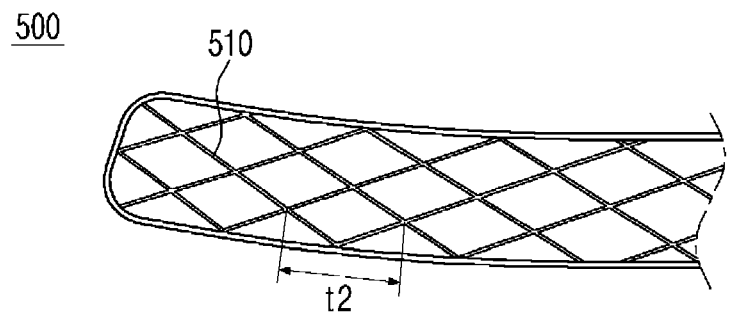
[Fig.17]
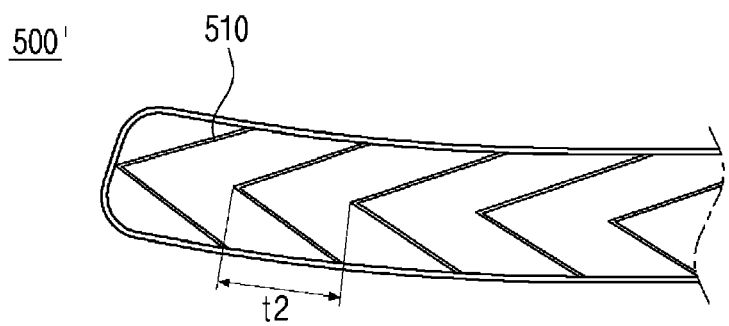
[Fig.18]
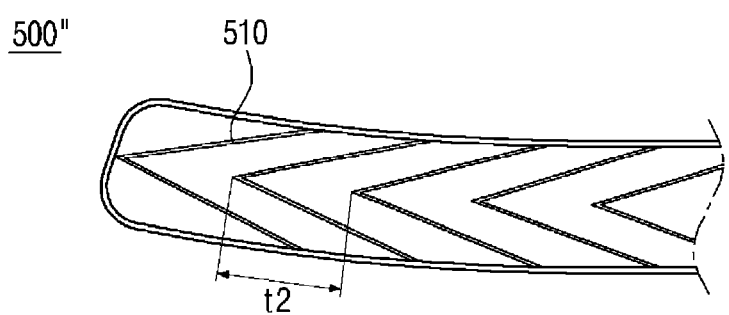

[Fig.19]
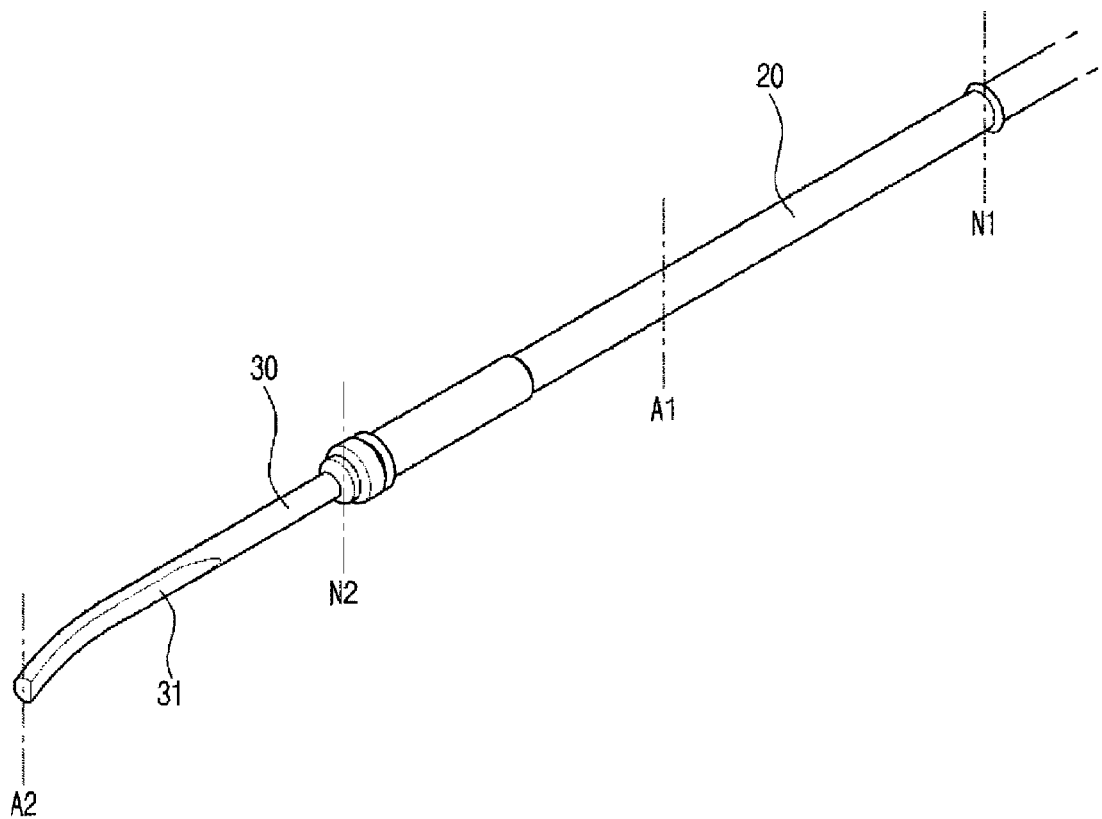
[Fig.20]
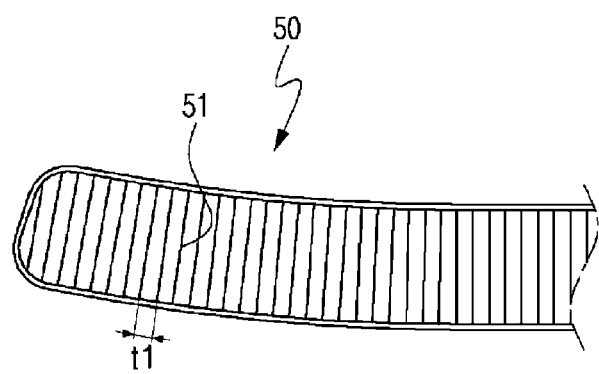

TOOL FOR SURGICAL OPERATION USING ULTRASONIC WAVES

INCORPORATION BY REFERENCE TO ANY PRIORITY APPLICATIONS

This application is the U.S. National Phase of International Application No. PCT/KR2012/001183, filed Feb. 16, 2012, designating the U.S. and published in Korean as WO 2013/122274 on Aug. 22, 2013, which is hereby incorporated by reference in its entirety.

SUMMARY

The present invention relates to a tool for a surgical operation using ultrasonic waves, and more particularly, to a tool for surgical operation using ultrasonic waves, which can more rapidly and effectively perform cutting and hemostasis by ensuring a maximum active length while maximizing ultrasonic wave strength by ensuring a maximum value of a gain step.

BACKGROUND ART

These days, instruments that perform a surgical operation by using ultrasonic waves have been gradually developed. A representative tool for surgical operation used in laparoscopic surgery among them is Harmonic Scalpel disclosed in Japanese Patent No. 4307890.

However, in the case of the Harmonic Scalpel in the related art, which is disclosed in Japanese Patent No. 4307890, a maximum value which a gain step can have in order to ensure a maximum active length cannot be ensured, and as a result, ultrasonic wave strength cannot be maximized.

That is, in the tool for surgical operation using the ultrasonic waves, such as the Harmonic Scalpel in the related art, the active length and the gain step are determined as contrary components, and as a result, only an instrument performing the surgical operation, which can perform cutting and hemostasis by selecting only any one of both components according to a surgical site has been developed.

DISCLOSURE

Detailed Description of Certain Embodiments

A technical object of the present invention is to provide a tool for surgical operation using ultrasonic waves, which can more rapidly and effectively perform cutting and hemostasis by ensuring a maximum active length while maximizing ultrasonic wave strength by ensuring a maximum value which a gain step can have.

Technical objects to be solved by the present invention are not limited to the aforementioned technical object and other unmentioned technical objects will be clearly understood by those skilled in the art from the following description.

Technical Solution

An exemplary embodiment of the present invention provides a tool for surgical operation using ultrasonic waves, the tool including: a transducer generating ultrasonic waves; a transmitting rod having a cylindrical bar shape and transmitting the ultrasonic waves generated by the transducer to one end portion from the other end portion connected with the transducer; an end effector that extends from one end portion of the transmitting rod and cuts a surgical site by using the ultrasonic waves received from the transmitting rod in which a part of a circular cross-section area is formed to be flat from a point corresponding to the second vibration node so that a gain step is started at the second vibration node most adjacent from one end portion of the transmitting rod; a rod cover covering the transmitting rod by using a plurality of vibration nodes formed when the ultrasonic waves are transmitted through the transmitting rod as connection points; and a jaw for holding the surgical site while engaged with the end effector, which is combined to one end portion of the rod cover in a pivotable manner and is positioned to face the end effector.

In this case, an interval corresponding to the gain step may be a distance up to a second vibration anti-node positioned at a position spaced apart by a distance which is ¼ larger than the length of a wavelength for one cycle of the ultrasonic waves generated from the transducer in a direction opposite to a direction in which the transducer is connected from the second vibration node.

Here, when a frequency of the ultrasonic waves generated from the transducer is set to 55.5 kHz and the transmitting rod is made of cylindrical titanium, the gain step may become 20 mm and an active length which is cut while contacting the surgical site may become 15 mm.

Meanwhile, a part of the cross-sectional area of the end effector which is flat may be divided into a first surface and a second surface around the center of the other surface of the end effector and both the first surface and the second surface may be provided on the other surface opposite to one surface of the end effector contacting the jaw.

In this case, the first surface and the second surface may be tilted toward both sides between one surface and the other surface of the end effector at the center of the other surface of the end effector in opposite directions to each other.

Further, the first and second surfaces may be consecutively formed in a longitudinal direction which extends from the second vibration node to the second vibration anti-node, and tilts of the first and second surfaces may increase toward the second vibration anti-node.

Further, the first surface and the second surface may be symmetric to each other to have the same area and the same tilt.

Meanwhile, a part of the cross-sectional area of the end effector which is flat may be divided into a third surface and a fourth surface around the center of the other surface of the end effector and the third surface may be provided on the other surface opposite to one surface of the end effector contacting the jaw and the fourth surface may be provided on one side between one surface and the other surface of the end effector.

In this case, the third surface may be tilted toward the other side between one surface and the other surface of the end effector opposite to one side of the end effector where the fourth surface is provided at the center of the other surface of the end effector.

Further, the third surface may be consecutively formed in a longitudinal direction which extends from the second vibration node to the second vibration anti-node, and a tilt of the third surface may increase toward the second vibration anti-node.

Further, the fourth surface may have the same cross-sectional length vertically to the other surface of the end effector and may be consecutively formed in a longitudinal direction that extends from the second vibration node to the second vibration anti-node.

Meanwhile, the jaw may include a tissue contacting surface and the tissue contacting surface has grooves formed on the tissue contacting surface forming one surface of the end effector at a predetermined interval in order to prevent the surgical site held while engaged with the end effector from being deviated, and the grooves may be angled in a longitudinal direction of the jaw based on a direction vertical to the longitudinal direction of the jaw.

Here, the grooves may be angled at 10° to 80° in the longitudinal direction of the jaw when an angle in the direction vertical to the longitudinal direction of the jaw is 0°.

Furthermore, the grooves may be provided on the inner surface of the jaw in a lattice shape or provided in a symmetric bent shape toward both sides from the center of the inner surface of the jaw.

Meanwhile, the tool may further include an actuating unit controlling the ultrasonic waves generated from the transducer and controlling motions of the rod cover and the jaw, in which the actuating unit may be included in a part of a control unit constituting a computer-integrated robotic surgery system and the motions of the rod cover and the jaw may be complexly automatically controlled together with other tools for surgical operation included in the computer-integrated robotic surgery system.

Advantageous Effects

According to a tool for surgical operation using ultrasonic waves in accordance with the present invention, cutting and hemostasis can be more rapidly and effectively performed by ensuring a maximum active length while maximizing ultrasonic wave strength by ensuring a maximum value which a gain step can have.

DESCRIPTION OF DRAWINGS

FIG. 1 is a perspective view illustrating an exemplary embodiment of a tool for surgical operation using ultrasonic waves according to the present invention.

FIG. 2 is an enlarged perspective view illustrating one end of a transmitting rod and an end effector in the exemplary embodiment of the tool for surgical operation using ultrasonic waves according to the present invention.

FIG. 3 is an enlarged perspective view illustrating one end of the transmitting rod and the end effector in the exemplary embodiment of the tool for surgical operation using ultrasonic waves according to the present invention in another direction.

FIG. 4 is a cross-sectional view taken along line C0 in FIGS. 2 and 3.

FIG. 5 is a cross-sectional view taken along line C1 in FIGS. 2 and 3.

FIG. 6 is a cross-sectional view taken along line C2 in FIGS. 2 and 3.

FIG. 7 is a cross-sectional view taken along line C3 in FIGS. 2 and 3.

FIG. 8 is a cross-sectional view taken along line C4 in FIGS. 2 and 3.

FIG. 9 is a cross-sectional view taken along line C5 in FIGS. 2 and 3.

FIG. 10 is a cross-sectional view taken along line C6 in FIGS. 2 and 3.

FIG. 11 is a cross-sectional view illustrated to correspond to FIG. 4, when one end of the transmitting rod and the end effector are modified in the exemplary embodiment of the tool for surgical operation using ultrasonic waves according to the present invention.

FIG. 12 is a cross-sectional view illustrated to correspond to FIG. 5, when one end of the transmitting rod and the end effector are modified in the exemplary embodiment of the tool for surgical operation using ultrasonic waves according to the present invention.

FIG. 13 is a cross-sectional view illustrated to correspond to FIG. 6, when one end of the transmitting rod and the end effector are modified in the exemplary embodiment of the tool for surgical operation using ultrasonic waves according to the present invention.

FIG. 14 is a cross-sectional view illustrated to correspond to FIG. 7, when one end of the transmitting rod and the end effector are modified in the exemplary embodiment of the tool for surgical operation using ultrasonic waves according to the present invention.

FIG. 15 is a cross-sectional view illustrated to correspond to FIG. 8, when one end of the transmitting rod and the end effector are modified in the exemplary embodiment of the tool for surgical operation using ultrasonic waves according to the present invention.

FIG. 16 is a plan view illustrating an example of one surface of a jaw contacting the end effector in the exemplary embodiment of the tool for surgical operation using ultrasonic waves according to the present invention.

FIG. 17 is a plan view illustrating a modified example of one surface of the jaw contacting the end effector in the exemplary embodiment of the tool for surgical operation using ultrasonic waves according to the present invention.

FIG. 18 is a plan view illustrating another modified example of one surface of the jaw contacting the end effector in the exemplary embodiment of the tool for surgical operation using ultrasonic waves according to the present invention.

FIG. 19 is an enlarged perspective view illustrating one end of a transmitting rod and an end effector in a tool for surgical operation using ultrasonic waves in the related art.

FIG. 20 is a plan view illustrating one surface of a jaw contacting the end effector in the tool for surgical operation using ultrasonic waves in the related art.

Hereinafter, exemplary embodiments of the present invention will be described in detail with reference to the accompanying drawings. However, in describing the present invention, a detailed description of already known functions or configurations will be omitted so as to make the subject matter of the present invention clear.

An exemplary embodiment of a tool for surgical operation using ultrasonic waves according to the present invention is configured to include a transducer 100, a transmitting rod 200, an end effector 300, a rod cover 400, and a jaw 500, as illustrated in FIGS. 1 to 18.

Herein, the transducer 100 is a component generating ultrasonic waves by receiving an electric signal capable of generating the ultrasonic waves from an input terminal 120 (however, in FIGS. 1 to 18, circuits, electric wires, and the like for transmitting a signal between the transducer 100 and the input terminal 120 are not illustrated).

A frequency of the ultrasonic waves generated by the transducer 100 varies depending on conditions of the transmitting rod 200 and the end effector 300 to be described below. That is, the transducer 100 generates optimal ultrasonic waves according to a shape and a material of the transmitting rod 200 or designs of a gain step and an active length which may be generated in the end effector 300.

For example, if it is designed that the transmitting rod 200 is made of cylindrical titanium, the gain step which may be generated in the end effector 300 is set to approximately 20 mm, and the active length is set approximately 15 mm, the transducer 100 is set to generate ultrasonic waves having a frequency of approximately 55.5 kHz.

Further, the strength (amplitude and displacement) of the ultrasonic waves generated by the transducer 100 may be controlled through a second switch 630 to be described below by considering a surgical site to be cut.

For example, in the case where the surgical site is a portion which is formed by a thick tissue or through which blood vessels pass, the strength of the ultrasonic waves is controlled to increase and in other portions, the strength of the ultrasonic waves is controlled to decrease so as to prevent the operation from being disturbed by a by-product generated upon cutting.

Meanwhile, the transmitting rod 200 serves to transmit the ultrasonic waves generated by the transducer 100 to the end effector 300 by connecting the transducer 100 and the end effector 300.

The transmitting rod 200 may have a cylindrical bar shape which is thin and long so that the end effector 300 is inserted into a hole formed in a trocar used in laparoscopic surgery to reach the surgical site.

In this case, the length of the transmitting rod 200 may be a length suitable for a user to perform the laparoscopic surgery, but may be a length which is as large as a vibration node (means a point where the strength of the ultrasonic waves is substantially 0) of the ultrasonic waves generated by the transducer 100 and a vibration anti-node (means a point where the strength of the ultrasonic waves is substantially maximum as a concept contrary to the vibration node) may be repeated multiple times. Further, it is apparent that a fact that an interval corresponding to the gain step of the end effector 300 according to the present invention may become a distance corresponding to a cycle which is ¼ as long as the ultrasonic waves should be considered as described below.

In addition, the transmitting rod 200 may be made of various materials, but as illustrated above, the transmitting rod 200 may be advantageously made of a titanium material in order to effectively transmit the frequency of 55.5 kHz generated by the transducer 100.

Meanwhile, the end effector 300 is configured to perform cutting or hemostasis of the surgical site by using the ultrasonic waves and the end effector 300 is provided at one end portion of the transmitting rod 200 to perform cutting or hemostasis of a surgical site by receiving the ultrasonic waves generated by the transducer 100.

Since the end effector 300 uses the ultrasonic waves, the end effector 300 need not be unconditionally sharp unlike general cutting tools. That is, the end effector 300 is formed to perform cutting or hemostasis of the surgical site by using vibration energy and thermal energy generated by the ultrasonic waves, and as a result, the end effector 300 is effective in cutting or performing hemostasis of the surgical site through which the blood vessels pass.

For example, the end effector 300 may be formed to extend from one end portion of the transmitting rod 200 as illustrated in FIGS. 1 to 18 and the end effector 300 may cut the surgical site with the vibration energy and the thermal energy by compressing the surgical site together with a jaw 500 to be described below, which is provided at an opposite thereto.

Since the end effector 300 should be able to cut the surgical site by using the ultrasonic waves received from the transmitting rod 200, the end effector 300 should have the gain step (means that amplification rate is substantially 1 or more).

In this case, the shape and the structure of the end effector 300 may be diversified as a method for the end effector 300 to have the gain step, and in the present invention, a dimension of a transverse cross-sectional area of the end effector 300 is smaller than that in the vibration node to amplify energy of the ultrasonic waves according to a transverse cross-sectional area ratio. Accordingly, when the end effector 300 is formed to extend from the transmitting rod 200, a cross-sectional area is decreased by flattening a part of a circular cross-sectional area to form the gain step.

Meanwhile, in forming the end effector 300, it is important as much as the end effector 300 is formed to have the gain step is how large active length the end effector 300 has. That is, in the end effector 300, although the gain step is formed to amplify the energy of the ultrasonic waves, if the active length is small, in other words, if the ultrasonic waves may not have strength to substantially cut the surgical site, the end effector 300 is meaningless to the user who intends to cut the surgical site.

In order to ensure the active length having the important meaning, a point where the gain step is started and the vibration node are configured to be spaced apart from each other by 5% or more so as to maximally ensure the active length as illustrated in FIG. 19 in the related art. (In this case, a description of the tool for surgical operation using the ultrasonic waves in the related art is not contents mentioned in Japanese Patent No. 4307890 mentioned in Background Art, but the description is contents which can be apparently verified from a product widely used by doctors who actually perform the surgical operation.).

That is, in the tool for surgical operation using the ultrasonic waves in the related art, the cross-sectional area of even the end effector 30 is decreased by flattening a part of the circular cross-sectional area to form the gain step, but the point where the gain step is started and the vibration node is configured to be spaced apart from each other by a distance therebetween of 5% or more.

Accordingly, in the tool for surgical operation using the ultrasonic waves in the related art, in the end effector 300, a point where the gain step is ended may not be formed up to a point which a maximum amplitude (displacement) of the ultrasonic waves shown in the vibration anti-node reaches and this represents that a maximum value of the gain step is abandoned in order to ensure the maximum active length.

However, in the exemplary embodiment of the tool for surgical operation using the ultrasonic waves according to the present invention, the end effector 300 is configured so that the maximum active length may be ensured while ensuring the maximum value of the gain step by making the point where the gain step is started coincide with the vibration node.

That is, in the exemplary embodiment of the tool for surgical operation using the ultrasonic waves according to the present invention, if the end effector 300 is configured as described below, an interval corresponding to the gain step and a length corresponding to the maximum active length may similarly be a distance up to a second vibration anti-node A2 positioned at a position spaced apart by a distance which is ¼ larger than the length of a wavelength for one cycle of the ultrasonic waves generated from the transducer 100 in a direction opposite to a direction in which the transducer 100 is connected from a second vibration node N2.

First, when one example of the end effector 300 illustrated in FIGS. 2 to 10 is described, a part of a flat cross-sectional area of the end effector 300 may be configured to be divided into a first surface 310 and a second surface 320 around the center of the other surface (an opposite surface to one surface of the end effector 300 contacting the jaw 500) of the end effector 300.

Herein, both the first surface 310 and the second surface 320 may be provided on the other surface of the end effector 300 and the first and second surfaces 310 and 320 may be tilted toward both sides between one surface and the other surface of the end effector 300 at the center of the other surface of the end effector 300 in opposite directions to each other, similarly as a shape of the bottom of a ship.

In this case, the first and second surfaces 310 and 320 may be consecutively formed in a longitudinal direction which extends from the second vibration node N2 to the second vibration anti-node A2, and may be configured in such a manner that a slope increases toward the second vibration anti-node A2.

In more detail, the first and second surfaces 310 and 320 are constituted as one same surface at the center of the other surface of the end effector 300 as illustrated in FIG. 4 in the second vibration node N2, but the first and second surfaces 310 and 320 are configured to be gradually largely tilted toward both sides at the center of the other surface of the end effector 300 as illustrated in FIGS. 5 to 7 toward the second vibration anti-node A2.

The first and second surfaces 310 and 320 configured as above may be configured in parallel to each other as illustrated in FIGS. 8 to 10 when the first and second surfaces 310 and 320 are adjacent to the second vibration anti-node A2 and although a part of the end effector 300 adjacent to the vibration anti-node A2 is curved for convenience of the surgery, the first and second surfaces 310 and 320 may maintain the same shape without a change in configuration thereof.

Further, the first surface 310 and the second surface 320 may be symmetric to each other so as to have the same area and the same tilt. In this case, although the first surface 310 and the second surface 320 are configured to be asymmetric to each other, the first surface 310 and the second surface 320, of course, do not depart from the scope of the present invention and in the case where the first surface 310 and the second surface 320 are configured to be symmetric to each other, the ultrasonic waves will better proceed to one surface of the end effector 300 contacting the jaw 500.

Subsequently, when a modified example of the end effector 300 illustrated in FIGS. 11 to 15 is described, a part of the flat cross-sectional area of the end effector 300 may be configured to be divided into a third surface 330 and a fourth surface 340 around the center of the other surface (an opposite surface to one surface of the end effector 300 contacting the jaw 500) of the end effector 300.

Herein, the third surface 300 is a surface provided on the other surface of the end effector 300 contacting the jaw 500 and the fourth surface 340 is a surface provided on one side between one surface and the other surface of the end effector 300.

In more detail, the third surface 330 is a surface that is tilted toward the side of the end effector 300 at the center of the other surface of the end effector 300 similarly as the first surface 310 of one example of the end effector 300 illustrated in FIGS. 2 to 10 as described above and is consecutively formed with the tilt increased toward the second vibration anti-node A2 from the second vibration node N2.

However, the fourth surface 340 is a surface that has the same cross-sectional length vertically to the other surface of the end effector 300 unlike one example of the end effector 300 illustrated in FIGS. 2 to 10 as described above and is consecutively formed without a change in tilt up to the second vibration anti-node A2 from the second vibration node N2.

That is, as verified from FIGS. 11 to 15, the modified example of the end effector 300 is configured to be consecutively formed from the second vibration node N2 to the second vibration anti-node A2 with the change in slope on only one side between both sides between one surface and the other surface of the end effector 300.

In this case, one side whose tilt is changed, that is, the third surface 330 may be one side in a direction corresponding to a direction in which a part of the end effector 300 adjacent to the second vibration anti-node A2 bent for the convenience of the surgery, but the present invention is not limited thereto.

When the modified example of the end effector 300 is configured as above, the modified example is just different from one example of the end effector 300 illustrated in FIGS. 2 to 10 as described above in regarding whether the ultrasonic waves better proceeding to one surface of the end effector 300 contacting the jaw 500 and both examples are not different from each other in providing the tool for surgical operation using the ultrasonic waves, which can more rapidly and effectively perform cutting and hemostasis by ensuring the maximum active length while maximizing the strength of the ultrasonic waves by ensuring the maximum value of the gain step which is the technical object to be solved by the present invention.

Meanwhile, the rod cover 400 is configured to cover the transmitting rod 200 in order to protect transmitting of the ultrasonic waves through the transmitting rod 200.

It is preferable that the rod cover 400 does not contact the transmitting rod 200, but the rod cover 400 needs to be connected while contacting the transmitting rod 200 in the case where the transmitting rod 200 is long. In this case, any point is not used as a connection point, but it is preferable that a plurality of vibration nodes (for example, the second vibration node N2 and the first vibration node N1) where the ultrasonic waves are formed through the transmit node 200 is used as the connection point.

The reason is that in terms of a non-vibration node, since the intensity is not 0 (zero), and in terms of the non-vibration node, when the transmitting rod 200 and the rod cover 400 are connected to each other, a small amount of ultrasonic waves transmitted through the transmitting rod 200 is transmitted to the rod cover 400 to be lost.

Meanwhile, the jaw 500 is disposed at the position facing the end effector 300 to serve to hold the surgical site while engaged with the end effector 300.

If there is no jaw 500, there is no component supported when the end effector 300 is pushed in order to cut the surgical site, and as a result, the surgical site is pushed out and may not be cut well. That is, the jaw 500 is a configuration to cut the surgical site by assisting the end effector 300.

The jaw 500 playing the role may be configured to be coupled with the transmitting rod 200, but since the transmission of the ultrasonic waves to the end effector 300 may be interrupted, the jaw 500 is advantages to be configured to be coupled with one end of the rod cover 400.

Further, in order to easily hold or release the surgical site, the jaw 500 may be configured to be pivotably coupled with the rod cover 400, and may be configured to be interlocked with the first switch 620 so as to be easily controlled by the user.

In addition, the jaw 500 may have grooves 510 formed on the inner surface facing one surface of the end effector 300 at predetermined intervals, so as to prevent the surgical site held while engaged with the end effector 300 from being deviated.

In this case, the grooves 510 may be configured to be angled in a longitudinal direction of the jaw 500 based on a vertical direction to the longitudinal direction of the jaw 500.

That is, in the jaw 500, when a parallel direction with the direction in which the second vibration node N2 and the second vibration anti-node A2 are connected to each other is referred to as the longitudinal direction, if a slope in the vertical direction to the longitudinal direction is 0°, the grooves 510 may be formed to be angled at a predetermined angle in the longitudinal direction of the jaw 500.

In other words, when the predetermined angle is small, the grooves 510 may be formed in the vertical direction to the longitudinal direction of the jaw 500, and when the predetermined angle is large, the grooves 510 may be formed in the longitudinal direction of the jaw 500.

In this case, since the shape of the inner surface of the jaw 500 is close to a rectangle, the range of the predetermined angle may be 0° to 90°. However, as illustrated in FIG. 20 described below, in order to verify the difference on the effect from the grooves 51 formed on the inner surface of the jaw 500 of the tool for surgical operation using the ultrasonic waves in the related art, the angle needs to be 10° or more, and in order that the held surgical site is not slid in a holding direction, the angle is advantageously 80° or smaller.

As such, when the grooves 510 are angled at the predetermined angle, the grooves 510 may not be limited to the shapes thereof. However, for example, referring to the drawing for more detailed description, the grooves 510 may have a grid shape on the inner surface of the jaw 500 as illustrated in FIG. 16.

The end effector 300 and the jaw 500 have an advantage of increasing the holding force when holding the surgical site, but grooves 510 having the shape has a difficulty to manufacture, and may have a shape of a modified example illustrated in FIG. 17 or FIG. 18. That is, as illustrated in FIG. 17 or FIG. 18, grooves 510' and 510" may have a symmetric bent shape toward both sides from the center of the inner surface of the jaw 500.

When the jaw 500 is configured as described above, it is possible to solve a problem that may be generated when the surgical site is held by the jaw 500 of the tool for surgical operation using the ultrasonic waves in the related art having the grooves 51 as illustrated in FIG. 20.

That is, when the surgical site is held by the jaw 500 of the tool for surgical operation using the ultrasonic waves in the related art having the grooves 51 as illustrated in FIG. 20, the held surgical site may be aggregated in a holding direction to interrupt the end effector 300 cutting and cauterizing the surgical site.

However, when the surgical site is held by the jaw 500 of the tool for surgical operation using the ultrasonic waves according to the present invention, the held surgical site may be aggregated in a both side direction of the jaw 500, not the holding direction not to interrupt the end effector 300 cutting and cauterizing the surgical site, and as a result, the surgical site may be more rapidly and effectively cut and cauterized.

In addition, since the tool for surgical operation using the ultrasonic waves in the related art does not ensure a maximum value of a gain step in order to ensure a maximum operation length, only when the holding force of the surgical site between the end effector 300 and the jaw 500 is large, the cutting and cauterizing may be performed. As a result, as illustrated in FIG. 20, the holding force needs to be increased by making an interval t1 of the grooves 51 dense.

However, while ensuring the maximum operation length, the tool for surgical operation using the ultrasonic waves according to the present invention ensures the maximum value of the gain step, and as a result, the holding force may be small as compared with the tool for surgical operation using the ultrasonic waves in the related art, thereby increasing an interval t2 of the grooves 510.

As such, when the interval t2 of the grooves 510 is increased, it is natural to require smaller efforts and costs when manufacturing the inner surface of the jaw 500.

Meanwhile, an actuating unit 600 is a component to control the transducer 100 and adjust the motion of the rod cover 400 and the jaw 500, and may be variously configured according to convenience of the user.

For example, in the exemplary embodiment of the tool for surgical operation using the ultrasonic waves according to the present invention, the actuating unit 600 may be configured by a handle 610, a first switch 620, a second switch 630, and a third switch 640.

Here, the handle 610 may be configured to be similar to a grip of a handgun so as the user to easily perform the operation by holding the tool for surgical operation using the ultrasonic waves according to the present invention with one hand and bringing the end effector 300 at the surgical site.

Further, the first switch 620 may be configured to turn on/off the transducer 100 to generate the ultrasonic waves and move the jaw 500 to hold and cut the surgical site together with the end effector 300.

Further, the second switch 630 may be configured to control the intensity of the ultrasonic waves generated from the transducer 100, and the third switch 640 may be configured to rotate the rod cover 400 for an index finger of the user to rotate the end effector 300 or/and the jaw 500.

Meanwhile, the tool for surgical operation using the ultrasonic waves according to the present invention is directly used by hand power when the user operates, but the present invention is not limited thereto, and it is natural that the present invention may be extended and used in an automatic robot in which the tool for surgical operation is installed.

In more detail, for example, the actuating unit 600 may be considered to be included in a part of a control unit (not illustrated) constituting a computer-integrated robotic surgery system, and as such, in the case of constituting the actuating unit 600, the actuating unit 600 needs not to be configured by the handle 610, the first switch 620, the second switch 630, and the third switch 640.

That is, when the actuating unit 600 is included in the part of the control unit (not illustrated) constituting the computer-integrated robotic surgery system, the motion of the rod cover 400 and the jaw 500 may be complexly automatically controlled together with other tools for surgical operation included in the computer-integrated robotic surgery system.

Although the specific exemplary embodiments have been described and illustrated as above, the present invention is not limited to the exemplary embodiments described herein, and it would be apparent to those skilled in the art that various changes and modifications might be made to these exemplary embodiments without departing from the spirit and the scope of the invention. Accordingly, the changed example and modified examples should not be individually appreciated from the technical spirit or the viewpoint of the present invention and it should be appreciated that modified exemplary embodiments will be included in the appended claims of the present invention.

What is claimed is:

1. A tool for surgical operation using ultrasonic waves, the tool comprising:
    a transducer generating ultrasonic waves;
    a transmitting rod having a cylindrical bar shape and transmitting the ultrasonic waves generated by the transducer to a distal end portion from a proximal end portion connected with the transducer;
    an end effector that extends from the distal end portion of the transmitting rod configured to perform cutting or hemostasis of a surgical site by using the ultrasonic waves received from the transmitting rod, wherein:
        a cross-sectional area of the end effector is substantially circular at a proximal portion adjacent the distal end of the transmitting rod;
        two symmetrical, non-parallel flat indentations extend longitudinally along the end effector from a point corresponding to a second vibration node to a point corresponding to a second vibration anti-node; and
        an angle between the symmetrical, non-parallel flat indentations decreases as the flat indentations extend longitudinally from the second vibration node to the second vibration anti-node until the flat indentations are parallel and disposed on opposite sides of the end effector at the second vibration anti-node, such that the cross-sectional area of the end effector decreases from the second vibration node to the second vibration anti-node;
    a rod cover covering the transmitting rod; and
    a jaw for holding the surgical site while engaged with the end effector, which is combined to one end portion of the rod cover in a pivotable manner and is positioned to face the end effector.

2. The tool of claim 1, wherein when a frequency of the ultrasonic waves generated from the transducer is set to 55.5 kHz and the transmitting rod is made of titanium, a gain step is 20 mm and an active length which will cut while contacting the surgical site is 15 mm.

3. The tool of claim 1, wherein the symmetrical, non-parallel flat indentations are provided on a surface opposite to a surface facing the jaw at the second vibration node and gradually rotate longitudinally to surfaces to sides of the surface facing the jaw at the second vibration anti-node.

4. The tool of claim 1, wherein the jaw includes a tissue contacting surface comprising grooves formed on the tissue contacting surface forming one surface of the end effector at a predetermined interval in order to prevent the surgical site held while engaged with the end effector from being deviated and the grooves are angled in a longitudinal direction of the jaw based on a direction vertical to the longitudinal direction of the jaw.

5. The tool of claim 4, wherein the grooves are angled at 10° to 80° in the longitudinal direction of the jaw when an angle in the direction vertical to the longitudinal direction of the jaw is 0°.

6. The tool of claim 5, wherein the grooves are provided on the inner surface of the jaw in a lattice shape or provided in a symmetric bent shape toward both sides from the center of the inner surface of the jaw.

7. The tool of claim 1, further comprising:
    an actuating unit controlling the ultrasonic waves generated from the transducer and controlling motions of the rod cover and the jaw.

8. A tool for surgical operation using ultrasonic waves, the tool comprising:
    a transducer generating ultrasonic waves;
    a transmitting rod having a cylindrical bar shape and transmitting the ultrasonic waves generated by the transducer to a distal end portion from a proximal end portion connected with the transducer;
    an end effector that extends from the distal end portion of the transmitting rod configured to perform cutting or hemostasis of a surgical site by using the ultrasonic waves received from the transmitting rod, wherein:
        a cross-sectional area of the end effector is substantially circular at a proximal portion adjacent the distal end of the transmitting rod;
        two asymmetrical, non-parallel flat indentations extend longitudinally along the end effector from a point corresponding to a second vibration node to a point corresponding to a second vibration anti-node;
        the non-parallel, asymmetrical flat indentations include a first surface opposite to a surface facing a jaw and a second surface on a side disposed between the first surface and the surface facing the jaw;
        an angle of the first surface with respect to the second surface decreases as the first surface extends longitudinally from the second vibration node to the second vibration anti-node; and
        an angle of the second surface is unchanged from the second vibration node to the second vibration anti-node;
    a rod cover covering the transmitting rod; and
    wherein the jaw is for holding the surgical site while engaged with the end effector, which is combined to one end portion of the rod cover in a pivotable manner and is positioned to face the end effector.

9. The tool of claim 8, wherein the first surface gradually rotates longitudinally from the surface opposite the surface facing the jaw at the second vibration node to a surface on a side opposing the second surface at the second vibration anti-node.

* * * * *